(12) United States Patent
Mitschke et al.

(10) Patent No.: US 6,715,918 B2
(45) Date of Patent: Apr. 6, 2004

(54) CALIBRATION PHANTOM FOR PROJECTION X-RAY SYSTEMS

(75) Inventors: Matthias Mitschke, Nürnberg (DE); Oliver Schuetz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/224,373

(22) Filed: Aug. 21, 2002

(65) Prior Publication Data

US 2003/0058999 A1 Mar. 27, 2003

(30) Foreign Application Priority Data

Aug. 21, 2001 (DE) .......................................... 101 40 867

(51) Int. Cl.$^7$ .............................................. G01D 18/00

(52) U.S. Cl. ........................................ 378/207; 378/163

(58) Field of Search ........................ 378/20, 162, 163, 378/164, 204, 207

(56) References Cited

U.S. PATENT DOCUMENTS

| | | | | |
|---|---|---|---|---|
| 4,818,943 A | * | 4/1989 | Chandra | 324/318 |
| 5,442,674 A | | 8/1995 | Picard et al. | 378/20 |
| 5,835,563 A | | 11/1998 | Navab et al. | 378/207 |
| 6,044,132 A | * | 3/2000 | Navab | 378/163 |

* cited by examiner

*Primary Examiner*—Edward J. Glick
*Assistant Examiner*—Courtney Thomas
(74) *Attorney, Agent, or Firm*—Young & Thompson

(57) ABSTRACT

A calibration phantom includes an arrangement of markings with a first X-ray absorption capability and a second X-ray absorption capability, with the arrangement of markings precluding superimposition of an image of a first marking with an image of a second marking for a sufficient number of successive markings for each projection condition, the physical embodiment of a marking representing a value assignment, and the value assignment of a respective specific first number of adjacent markings in each case forming first code information, with each of the first code information items being unique within the first code information which is formed in the totality of markings and in both reading directions.

17 Claims, 3 Drawing Sheets

CALIBRATION PHANTOM FOR PROJECTION X-RAY SYSTEMS

FIELD OF THE INVENTION

The present invention relates to an apparatus and a method for determining the projection geometry of X-ray apparatuses for recording radiographic projection images of objects and for representation of the objects, derived from this, with the aid of a reconstructive imaging method. In particular, the present invention relates to an apparatus for geometric calibration of mobile and stationary C-arc X-ray systems and of X-ray systems for tomosynthesis.

BACKGROUND OF THE INVENTION

Both in the case of C-arc X-ray systems and in the case of X-ray systems for tomosynthesis, an investigation object is located in the beam path between an X-ray source and a detector which is located opposite the X-ray source. The X-ray radiation which is emitted from the X-ray source is directed at the detector, so that the X-ray radiation passes through an object which is located between the X-ray source and the detector. The X-ray radiation is attenuated along each projection line as a function of the local X-ray absorption characteristics of the investigation object, on each of the projection lines between the X-ray source and the detector, so that this results in a distribution of the X-ray intensity on the detector surface which reflects the different attenuation of the X-ray radiation by the investigation object in the projection direction. The radiation which is received by the detector is converted to digital signals in order to produce a projection image.

A number of projection images are recorded in different projection conditions both for 3D reconstruction and for tomosynthesis. In tomosynthesis, a number of projection images are reconstructed on a focus plane, or else different projection images are combined to form a partially three-dimensional image. Tomosynthesis can be carried out on different X-ray systems, also including C-arc X-ray systems. In the case of C-arc X-ray systems, the radiation is normally passed through the investigation object from different angles and, in consequence, the investigation object is reconstructed in the form of a three-dimensional image from the projection images obtained in this way. This method is generally referred to as 3D reconstruction.

In comparison to computer tomography, C-arc X-ray systems are distinguished by having very short measurement times. C-arc X-ray systems are thus used by preference particularly when using contrast means which remain in the investigation area for only a short time, for example in angiography. In comparison to mobile C-arc X-ray systems, stationary C-arc X-ray systems are generally distinguished by shorter measurement times and a longer focal length. Mobile C-arc X-ray systems can be moved to an operating table both during and after operations, so that they are used especially for intraoperative investigation purposes and for monitoring records after completion of an operation.

In order to make it possible to make reliable statements about an object being investigated, geometrically exact reconstruction of the image representation of the object being investigated, with adequate position resolution and with a low artefact level, from the recorded projection images is essential. For 3D reconstruction on C-arc X-ray systems, a number of projection images or X-ray images are recorded at equidistant or variable angle increments, with the overall angle of the orbital rotation of the X-ray source and the detector located opposite it typically being 180° plus half the beam angle of the beam lobe emitted from the X-ray focus, together amounting to approximately 190°. A representation of high-contrast objects such as bones with sufficient position resolution and with a sufficiently low artefact level can be derived from only approximately 50 to 100 projection images. A greater number of X-ray images are required for better image quality of the isotropic 3D data cube which is derived from the projection images. In order, for example, to achieve better contrast resolution with a lower noise level and a lower artefact level, up to 200 records or more may be required in some cases. The precise number of X-ray images required for an investigation is not fixed, but depends on the respective specific requirements for each investigation.

The calculation of the data cube is dependent on knowledge of the projection geometry of each individual projection image. Apart from the physical design of the system, the individual projection geometries of a system are also influenced by the mechanical tolerances in manufacture and, in particular, by deforming influences resulting from the force of gravity on projecting parts of the system.

The recording geometry and the projection for each individual projection image can be described by a projection matrix. The projection matrix can be defined by imaging a defined calibration phantom and by looking for the appropriate structure in the X-ray image for each specially distinguished point in the calibration phantom. In the simplest case, specially distinguished points such as these are in the form of small stainless steel balls in the calibration phantom. If a sufficient number of correspondences are found between specially distinguished points in the calibration phantom and their images in the X-ray image, so-called 2D-3D correspondences, a projection matrix can be defined for the specific recording geometry of that X-ray image. The projection matrix produced in this way contains all the necessary information to describe the imaging geometry completely.

The calibration phantom which is disclosed in U.S. Pat. No. 5,835,563 comprises a ring with a low X-ray absorption capability, to whose circumference markings with a high X-ray absorption capability are applied. The calibration phantom is positioned in the system before a measurement, such that its image occupies only a subregion of the 2D projection image. The rest of the image area is available for imaging the object which is actually to be reconstructed. The projection matrix which is defined by this calibration phantom, which is referred to as a marker ring, for the image subregion can be transferred to the entire image area, although this can result in inaccuracies in the reconstruction of the data cube.

The mechanical stability of both stationary and mobile modern C-arc X-ray systems ensures a reproducible imaging and recording geometry over a lengthy time period. A calibration phantom therefore no longer need be imaged simultaneously with the investigation object in an X-ray record. Instead of this, the calibration can be carried out at relatively long time intervals off-line, that is to say separately from the recordings of an investigation object. The image area of the X-ray system is thus completely available for the actual object of the investigation.

In order to achieve the reconstruction of the isotropic data cube with the best possible resolution and accuracy, it is advantageous to distribute the markers uniformly over the entire 3D reconstruction volume.

For this purpose, U.S. Pat. No. 5,442,674 proposes a calibration phantom in the form of a hollow cylinder composed of plexiglass, in whose surface balls with a high X-ray absorption capability are incorporated along a helical line. The diameter, pitch and length of the helical line are designed such that the balls are distributed over the entire image area of the projection. One or more specially distinguished balls are designed to be somewhat larger than the others and are used as geometric reference points, from which the other marking balls can be identified by counting.

The specially distinguished balls are arranged in the center or close to the center of the helical line, so that the individual balls in the phantom can be identified even when the outer ends of the helical line are not also being imaged. If the images of one or more specially distinguished balls are superimposed during the recording of an image at a specific angle with the images of adjacent balls, then this makes it more difficult to identify the individual balls. The same is also often true for the superimposition of the images of adjacent balls. If the edge areas of the cylinder are not also imaged in the X-ray image, then an unknown number of balls will be missing from the helical line in the image, so that it is impossible to identify the balls in the image itself by counting, starting from one specially distinguished ball. In some cases, the information which is required for identification can be obtained only with increased computation complexity and with the assistance of identification information from preceding or subsequent projection images.

SUMMARY OF THE INVENTION

The object of the present invention is therefore to specify a calibration phantom which allows direct identification of each marking of the calibration phantom in each projection image of a projection X-ray system for 3D reconstruction and tomosynthesis.

This object is achieved by a calibration phantom for determining at least one projection geometry for X-ray apparatuses which are designed for recording radiographic projection images of objects for a representation of the objects which is derived from this with the aid of a reconstructive imaging method, with the calibration phantom having a support in the form of a defined volume body or hollow body and markings, which are applied in a linear arrangement to the surface and/or within the support, with the markings having a first X-ray absorption capability and the support having a second X-ray absorption capability, which is different to the first X-ray absorption capability, the linear arrangement of the markings precluding superimposition of an image of a first marking with an image of a second marking for a sufficient number of successive markings for each projection condition, with the physical embodiment of a marking representing a value assignment, and with the value assignments for a sequence of successive markings forming code information, and, furthermore, with a first number of successive markings forming a first type of code information such that each code information item of the first type occurs once, and only once, in both sequence directions of the markings, and is thus unique.

The object of the invention is furthermore achieved by a method for determining at least one projection geometry for an X-ray apparatus which is designed using a calibration phantom according to the invention for recording radiographic projection images of objects for a representation of the objects which is derived from this with the aid of a reconstructive imaging method, with the method having the following steps: the calibration phantom is placed in the projection area between the X-ray source and the detector, the projection images are recorded in different projection conditions, the position of each image of a marking in each projection image is determined, the code information is extracted from the images of the markings, that marking which causes the image is identified for each image of a marking with the aid of the extracted code information, and the parameters of the projection geometry are calculated from the association between the images of the markings and the position of the markings which cause them.

The above object is furthermore achieved by a calibration device for determining at least one projection geometry of an X-ray apparatus which is designed for recording radiographic projection images of objects for a representation of the objects which is derived from this with the aid of a reconstructive imaging method, with the calibration device having a calibration phantom according to the invention, a holding device for placing the calibration phantom in the projection area of the X-ray apparatus, and an evaluation device for carrying out the method according to the invention for determining the projection geometry.

In comparison to calibration of the projection geometry of projection X-ray systems using a marker ring, the calibration phantom according to the invention offers the advantage that qualitatively more accurate projection matrices can be calculated, thus allowing more reliable 3D reconstruction. This considerably reduces the level of the artefacts in the 3D reconstructions. A further advantage is that the calibration phantom according to the invention is very simple to place in X-ray systems since it is irrelevant what part of the arrangement of markings is imaged in the projection image. The identity of each individual marking of any given segment element of the marking arrangement can advantageously be determined from each projection image. The identification of the reading direction from the code information of adjacent markings also allows rotated positioning of the calibration phantom.

Further advantageous embodiments of the invention are defined in the corresponding dependent claims.

The value assignments of a second number of successive markings advantageously form a second type of code information, with each of the code information items of the second type furthermore advantageously occurring once, and only once, in one of the two sequence directions of the markings, and thus being unique. This allows optimization of the calibration processes in that the length and form of different code information items can be matched to the respective requirements of a calibration process.

The markings preferably have two different physical embodiments for one binary value assignment, so that the value assignment advantageously corresponds to the binary number system used in digital evaluation systems. The physical extent of a marking preferably represents the value-assigning physical embodiment of the marking, with a marking furthermore advantageously being in the form of a body with a spherical surface. This firstly results in the definition of a simple identification criterion which can easily be implemented in automatic identification systems, while secondly ensuring that each projection image of a marking is independent of the projection direction.

In one preferred embodiment, the support for the calibration phantom is cylindrical, with the symmetry of the support corresponding to the symmetry of the sequence of projection images. Furthermore, the markings are advantageously arranged along a helical line, so that the individual markings are never superposed in the projection direction.

The markings are preferably so closely adjacent that at least one code information item of the first type is imaged in a radiographic projection image, thus producing complete information about the position of the calibration phantom in the X-ray apparatus in one projection image. The extent of the physical distribution of the markings may also go beyond the projection area, at least in a dimension transversely with respect to the projection direction, so that the edge area of the cylinder, for which the markings are imaged very close to one another, does not appear in the projection image.

BRIEF DESCRIPTION OF THE DRAWING

The invention will be described in more detail in the following text using exemplary embodiments and with reference to the following figures.

DETAILED DESCRIPTION OF THE INVENTION

Figure 1:
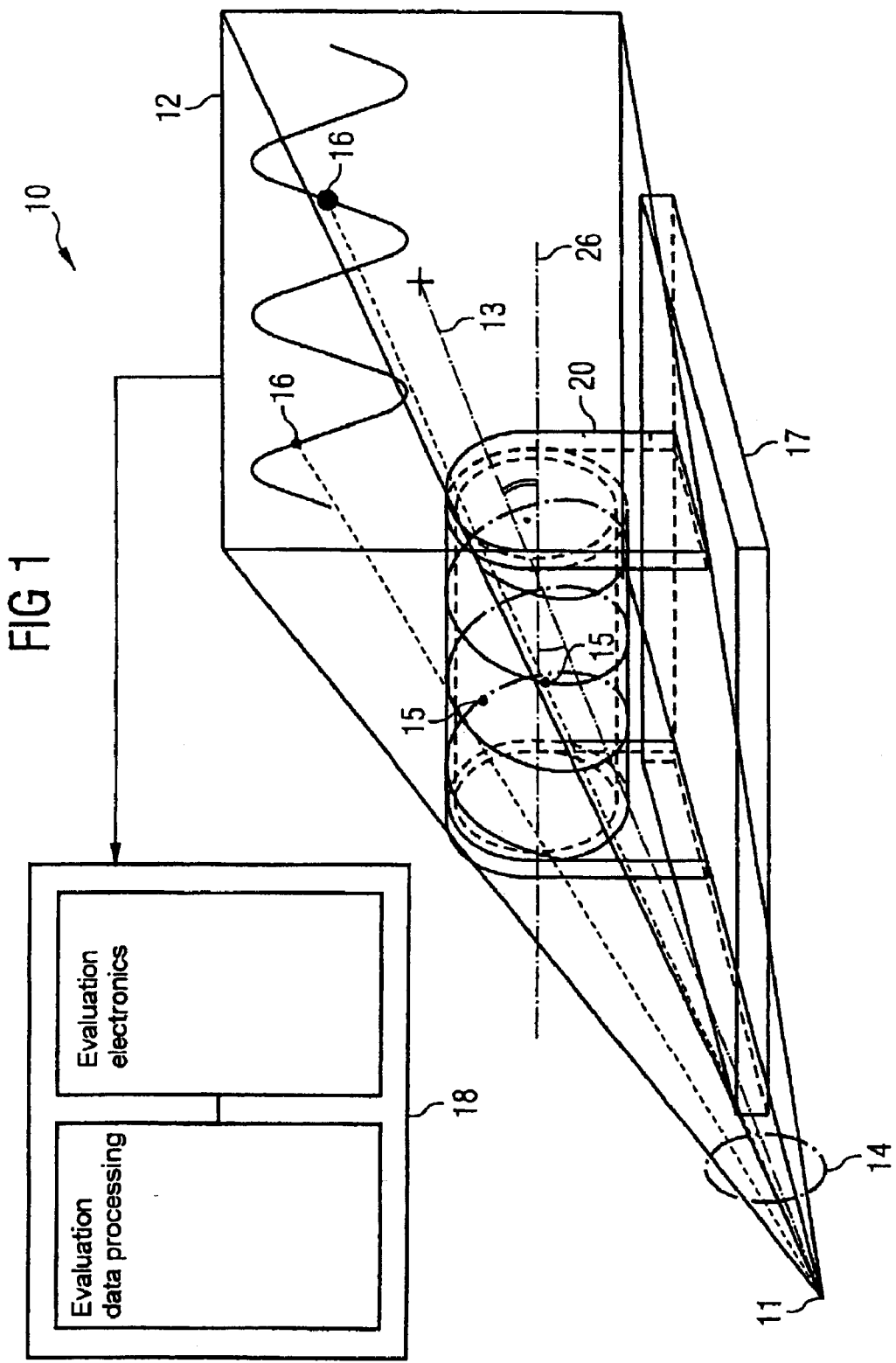
FIG. 1 shows, schematically, an X-ray apparatus with the geometry for producing a projection image of a calibration phantom according to the invention.

FIG. 1 shows the calibration phantom 20 positioned on a holding device 17 in the X-ray apparatus 10 between the focus of the X-ray source 11 and the detector 12 of the X-ray apparatus 10. The X-rays in the X-ray beam 14 emitted from the X-ray source focus 13 diverge, so that the X-ray beam has a conical shape. The cross-sectional area of the X-ray beam 14 increases as the distance from the focus 11 of the X-ray source increases, so that objects 15 of the same size produce images 16 of different size at different distances from the detector 12. The image signals supplied from the detector 12 are processed in the evaluation electronics in the evaluation device 18 and are evaluated in the evaluation data processing in this device 18, using one of the methods described below.

The base body 20 of the calibration phantom is preferably made of an X-ray-transparent material, such as plexiglass, carbon-fiber-reinforced plastic or the like, since this is the only way to ensure that all the markings which are applied on the base body are projected with sufficient image contrast onto the detector during a recording process.

The arrangement of the markings on the base body of the calibration phantom must satisfy the following requirements: for all projection conditions and projection directions of the X-ray apparatus, there must be no superimposition of images of individual markings in one projection image for a sufficient number of successive markings. Furthermore, the physical position of the markings in the calibration phantom must be known accurately, so that it is possible to determine the parameters of the image geometries exactly. The more precisely the markings are placed in the base body, the more exactly the 3D reconstruction can be carried out. An accuracy for the positioning of the markings of 0.05 mm can typically be achieved.

For significant imaging of the markings in the X-ray image, these markings are advantageously designed to be X-ray positive, using a material with a high X-ray absorption capability. The high image contrast which can be achieved in this way makes it possible to determine the position of the marking images in the projection images reliably. The markings may be made, for example, of stainless steel, lead, or similar materials.

Furthermore, the markings on the calibration phantom must have an accurately known geometric shape, for example being in the form of a ball or a cube or the like, so that the position of the centroid of the marking in the projection image can be determined accurately. The markings are ideally spherical since this always results in a solid circle in the projection image irrespective of the projection direction as the image of the marking, and the center of this circle coincides with the image of the centroid of the spherical marking.

In order to identify each individual marking, it must be possible to distinguish between them. This is achieved by using markings with different physical characteristics and a coded arrangement.

These physical characteristics must differ from one another sufficiently so that it is possible to distinguish between the shadow images of the markings, that is to say between the images of the markings in the respective projection images, in all projection conditions. Combinations or combination elements of spherical, cubic and bar-shaped markings are suitable, by way of example; however, in certain projection conditions, a combination of conical markings with spherical markings can lead to misinterpretation of the identity of the marking in the projection image, particularly when the projection is along a cone axis. However, since the use of non-spherical markings results in an increase in the complexity for determining the position of their centroid in the projection images, spherical markings are used exclusively in one preferred embodiment of the present invention. Distinguishable markings are in this case obtained by using balls of different size. In particular, it is preferable to use balls with two different sizes, thus achieving a marking form with a binary characteristic. Specific values are assigned to the different physical embodiments in order to identify the markings. In the following text, balls with a relatively small diameter are assigned the value 0, while balls with a relatively large diameter are assigned the value 1.

The criterion for the minimum size of the balls which are used as markings is the accuracy with which the center of the circular image of the balls can be determined in the projection image. The size difference between a ball with the value 0 and a ball with the value 1 is designed so as to ensure reliable identification of the value assigned to a marking in all projection conditions. The X-ray tubes which are used for projection image X-rays from a virtually point radiation source over a limited spatial angle so that the individual rays in the X-ray beam diverge. Markings on the calibration phantom which are located relatively close to the X-ray source are thus represented larger in the projection image than markings which are located closer to the detector, that is to say further away from the X-ray source. A large marking which is located close to the detector and has a relatively small image must now be distinguishable from a small marking close to the X-ray source, with a relatively large image. This condition is satisfied, by way of example, by markings whose small balls have a diameter of slightly less than about 2 mm and whose larger balls have a diameter of about 3.2 mm.

Figure 2:
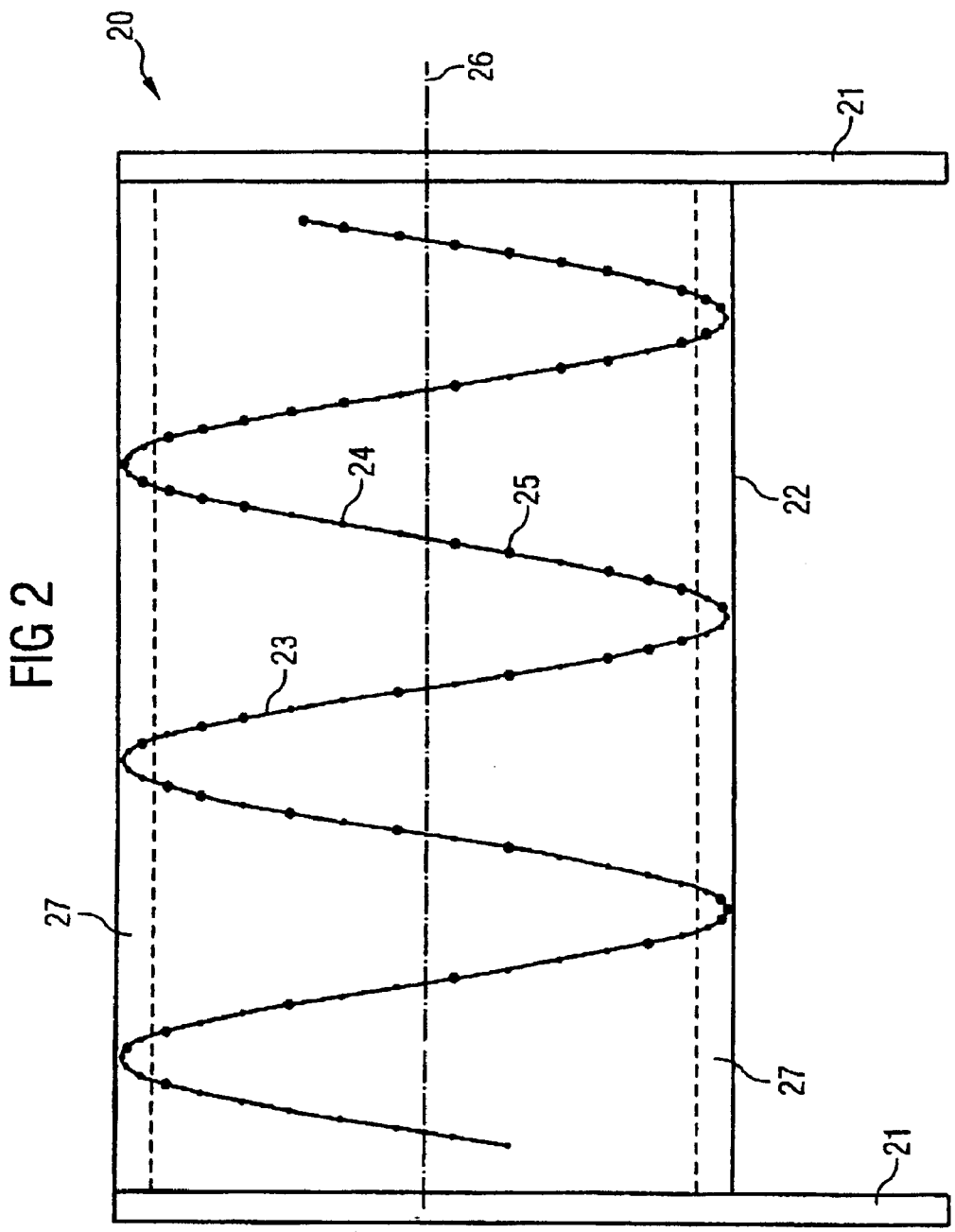
FIG. 2 shows a side view of a calibration phantom according to the invention.

FIG. 2 shows a side view of a calibration phantom 20 according to the invention, comprising a hollow cylinder 22 to each of whose two ends a stand foot 21 is fitted, on which the calibration phantom 20 is placed down. The hollow cylinder 22 and the stand feet 21 form the support or the base body for the calibration phantom. Instead of being equipped with a stand foot, the calibration phantom can be equipped with a receptacle for a holding device such as a stand, a hinge arm or the like, or may have no specific holding or standing apparatus. This is particularly advantageous if the aim is not to image any additional structures in the X-ray image, for example a base or an operating table.

The hollow cylinder 22 is made from material with a low X-ray absorption capability, while the stand feet 21 may be made from a material which is both X-ray positive and X-ray transparent. As an alternative to being in the form of a hollow cylinder 22, a solid cylinder may also be used for the calibration phantom.

In the example shown in FIG. 2, the markings 24 and 25 are applied on a helical line 23. The markings may be located not only on, but also partially or completely in, the material of the base body. The calibration phantom 20 is introduced into the beam path of the X-ray system such that the central projection ray 13 in the X-ray beam 14 is always approximately at right angles to the cylinder axis 26.

This ensures that a sufficient number of successive markings are not superimposed in the projection image, in all projection conditions. The only exception to this is the edge areas 27, at the upper and lower edge of the cylinder, as shown in FIG. 2, where the markers may be forced so closely together in the projection image that, in some circumstances, it is impossible to reliably prevent the image of one marking from being superimposed on the image of another marking. The diameter of the helix 23 or of the cylinder 22 is preferably chosen such that the outer areas 27 of the calibration phantom are located outside the projection area of the X-ray systems, so that no markings are superimposed in a projection image.

In the example in FIG. 2, the markings are arranged at equidistant angular increments on the helix. Alternatively, the markings may also be arranged with varying angular intervals, so that the density of the markings reflects special features in the achievable accuracy and in the projection geometry.

In order to make it possible to determine the imaging geometry, the 2D-3D correspondence of the markings is required, that is to say the position of the 2D image of a marking in the X-ray image and the 3D position of the corresponding marking in the calibration phantom. To achieve this, it must be possible to identify each individual marking on the calibration phantom in the X-ray image. For this purpose, large and small marking balls are distributed along the helix such that the sequence of markings includes a coding. In the preferred embodiment of a calibration phantom with marking balls of two different sizes, the coding is based on the binary system. Code information is obtained by considering a specific number of markings and noting small and large markings, and the sequence of zeros and ones associated with them, in one direction of the sequence.

Instead of being based on a binary system, the coding may also be based on a system with a higher base number, for example a ternary system with the numbers 0, 1 and 2, or even higher base numbers.

Figure 3:
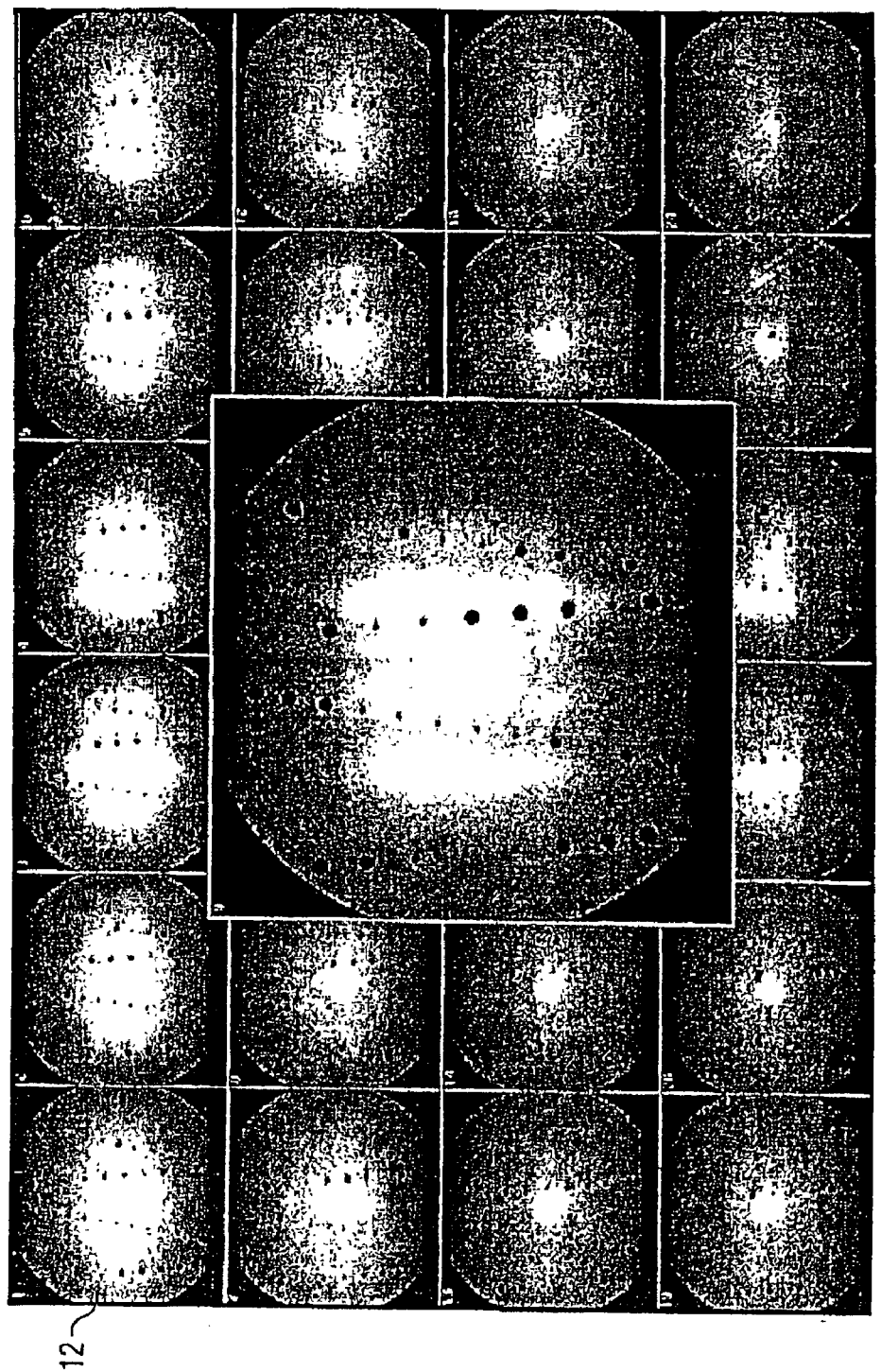
FIG. 3 shows a series of 2D projection images of the calibration phantom according to the invention.

The arrangement of the markings 24 and 25 on a helical line 23 surrounding the base body results in the images of the markings in the projection images being distributed over an approximately sinusoidal curve, as shown in FIG. 3. The diameter of the marking helix 23 is ideally larger than the projection area of the X-ray system, so that the markings which are located at the edge 27, that is to say at the upper and lower periphery of the cylinder 22, for the respective projection direction are not imaged in any projection image. The X-ray image of the calibration phantom thus does not contain any overlapping images of markings. If the diameter of the marking helix is chosen to be smaller or if the calibration phantom is not positioned optimally, an edge area of the helix will be imaged in the X-ray image. The markers which are superimposed in the edge area can be identified on the basis of their different shape by marker detection software, and can be excluded from the determination of corresponding 2D-3D correspondences.

If one considers the arrangement of markings on the calibration phantom from the viewpoint of a cohesive marker chain, then chain elements which are separated from one another of successive non-overlapping markings are imaged in the individual projection images. Since the marker chain represents a code sequence, the images of these chain elements may be regarded as code segments. The subdivision of the code sequence into individual code segments means that a marking coding must be used which allows unique identification of each marking in each chain element.

In one exemplary embodiment of the present invention, as is illustrated in FIG. 3, the marker chain is designed such that at least four chain elements or code segments, each having at least eight markings, are always imaged in each projection image. The coding thus advantageously represents an 8-bit code, that is to say eight adjacent markings in the marker chain always in each case form one 8-bit coded number or one 8-bit coded code information item, or one 8-bit coded code word. In order to ensure unique identification of the markings, the marker code is chosen such that each code word occurs only once in the entire marking chain.

If one code segment contains more than eight images of adjacent markings, then it also contains a number of code words. A coding with a short word length correspondingly results in a number of code information items within one code segment. In general:

$$A_K = 1 + (L_{KS} - L_W) \quad (1)$$

where $A_K$ is the number of code information items in a code segment with the bit length $L_{KS}$ for code information items with a bit length of $L_W$. Based on equation (1), four code information items are obtained for a code segment with a bit length of 11 and a code information item with a length of eight bits. An example of this is shown in the following Table 1:

TABLE 1

| 1 0 0 1 0 1 0 1 1 1 0 | Code segment |
|---|---|
| Code words obtained: | |
| 1 0 0 1 0 1 0 1 | first code word |
| 0 0 1 0 1 0 1 1 | second code word |
| 0 1 0 1 0 1 1 1 | third code word |
| 1 0 1 0 1 1 1 0 | fourth code word |

If, as required, and as illustrated in Table 1, each code word occurs once, and only once, in the entire code sequence of the marking chain, then it is also possible to identify an individual marking within an individual code word. This is dependent on the code sequence of the entire marking chain being known to the evaluator, or to the software for evaluation of the code information. This is because the position of the code word within the coding sequence is obtained from the code word that is read and, finally, the position of each marking within the code word, and hence also within the marker chain, is obtained from the construction of the code word.

There are now various options for developing a coding. By way of example, one analytical method starts with the start code word "1". This start code word is composed of a sequence of bits with the value 0, and a final bit with the value 1. The number of zeros in the code word is one less than its number of bits. The second code word may now be produced, for example, by shifting all the bits by one digit to the left in the start code word—this corresponds to multiplication by two—by ignoring the most significant bit and by producing the missing right-hand least significant bit using the following calculation rule:

| | |
|---|---|
| bit1(new) = bit4(old) XOR bit1(old) | 4 bit code |
| bit1(new) = bit5(old) XOR bit2(old) | 5 bit code |
| bit1(new) = bit6(old) XOR bit1(old) | 6 bit code |
| bit1(new) = bit7(old) XOR bit3 (old) | 7 bit code |
| bit1(new) = bit8(old) XOR bit4(old) XOR bit3(old) XOR bit4(old) | 8 bit code |
| bit1(new) = bit9(old) XOR bit4 (old) | 9 bit code |
| bit1(new) = bit10(old) XOR bit3 (old) | 10 bit code | where the following calculation rules apply for XOR:

1+0=1

0+1=1

0+0=0

1+1=0

The following series of the first six code words is obtained for the 4-bit code from the above calculation rule:

| | |
|---|---|
| Code word 1 | 0001 |
| Code word 2 | 0011 |
| Code word 3 | 0111 |
| Code word 4 | 1111 |
| Code word 5 | 1110 |
| Code word 6 | 1101 |

Since each code word in this series of code words also includes all the bits except for the most significant bit from the previous code word and only the least significant bit is in each case newly added, this sequence of code words can be represented in abbreviated form in a code word series which starts with the complete first code word and in which only the least significant bit is added on the right-hand side to each further code word in this series, so that this results in the following bit series from the above table:
000111101

Based on this form of representation, the following code series sequences are obtained from the calculation rules in Table 2:

| | |
|---|---|
| 000111101011001000 | 4 bit code |
| 00001010111011000111100110010000 | 5 bit code |
| 000011111101010011001101110110100100111000101 11100101000110 000100000 | 6 bit code |
| 00000010010011010011110111000011111110011101 110001010010111 110101010000101101111001110010101100110000011 01101011101000 110010001000000 | 7 bit code |
| 000000010110001111010000111111110010000101001 11110101010111 00000110001010110011001011111011110011011101 11001010100101 00010010110100011001110011110001101100001001 01110101111011 01111100001101001101011011010100000100111011 0 01001001100000 011101001000111000100000000 etc. | 8 bit code etc. |

These code sequences are used, without any further computation complexity, to additionally obtain two further code sequences, namely the inverse code in which all the zeros and ones are interchanged with one another, and the reflected code, which reflects the original code, read from back to front. The reflection of the code can also, of course, be applied to the inverse code, as well.

If the code series sequence is intended to have further additional characteristics, the described analytical method is difficult to use for generating a code series sequence.

It can be combined with or replaced by an experimental method. In this case, it is once again possible to start with a start value 1, but any other possible value is also feasible. The next subsequent code word can then be produced by shifting all the bits in the preceding code word by one digit to the left—that is to say multiply it by two—by ignoring the most significant bit and by filling the missing right-hand least significant bit both with a 0 and with a 1.

The two new code words which are produced in this way are then tested to determine whether they satisfy the additional requirements for the code series sequence. The next code word is defined using this method only for those code series sequences which satisfy the requirements as far as this stage in the development process. Code series sequences which no longer satisfy the requirements at any stage in the development process are rejected.

One of these requirements is the identification of the positioning of the calibration phantom in the X-ray apparatus. The cylindrical symmetry of the calibration phantom according to the invention results in two options for positioning the phantom, namely by interchanging the left-hand cylinder base surface with the right-hand cylinder base surface. In order to avoid errors in the localization of the marking, the marker code must therefore be designed such that the reading direction of the codes can be identified from the individual code words themselves. This means that the code words which are obtained when reading the code sequence in one direction from a first end of the code sequence to a second end of the code sequence do not occur when reading it in the opposite direction since, otherwise, this would lead to incorrect identification of markings. A code sequence which satisfies these conditions is referred to as a rotation-invariant code sequence.

A rotation-invariant 8-bit code sequence has a maximum possible length of 108 bits. A corresponding calibration phantom thus has 108 balls along the helical line, with the distribution of small and large balls corresponding to the distribution of zeros and ones in the code sequence, so that this results in a rotation-invariant 8-bit marker code. This marker correspondingly contains 108—7 code words in each reading direction, that is to say a total of 202 code words.

An 8-bit rotation-invariant code sequence with the maximum length may be designed, by way of example, as follows:
0000000100010100100110001001110000010101010110000 1011001010111 0001011101
10001111010011111010110110011101111111
The inverse code derived from this
1111111011101011011001110110001111101010100111110 100110101000 1110100010011
1000010110000010100100110001000000
the reflected code
1111111011100110110110101111001011110001101110100 0 111010100110 1000011010101
00000111001000110010010100010000000
and the inverse reflected code
00000001000110010010100000110100001110010001011 1000101011001 0111100101010
1111100011011100110110101011101111111
naturally also satisfy the requirements for a rotation-invariant 8-bit code sequence.

The first-mentioned rotation-invariant 8-bit code sequence results in the following code words in Table 3, with the table in each case showing only the first ten code words for the forward and backward reading directions.

| Forward marker code | Backward marker code |
|---|---|
| 00000001 | 10000000 |
| 00000010 | 01000000 |
| 00000100 | 00100000 |
| 00001000 | 00010000 |
| 00010001 | 10001000 |
| 00100010 | 01000100 |
| 01000101 | 10100010 |
| 10001010 | 01010001 |
| 00010100 | 00101000 |
| 00101001 | 10010100 |
| ... | ... |
| ... | ... |

A 7-bit rotation-invariant code has a maximum length of 46 characters. This allows 40 code words to be represented for one reading direction, that is to say a total of 80 code words.

The accuracy with which a projection geometry can be defined increases with the number of markings which are imaged in the X-ray image. However, as the number of markings in the calibration phantom increases, there is also an increase in the probability that the images of two markings will be superimposed in the X-ray image, so that they can no longer be used to determine the parameters of the imaging geometry. The production costs of the calibration phantom also, of course, increase as the number of markings increases. In order to determine the projection geometry with an accuracy of better than 0.2 mm, approximately 50 to 60 markings should be imaged in the X-ray image. Since the axial extent of the marking helix in the preferred embodiment of the present invention is larger than the imaging area, even more than 60 markings are required, so that at least one 8-bit rotation-invariant code is necessary.

Based on an 8-bit rotation-invariant code, at least three or four chain elements, each having at least 8 markings, must be imaged in the X-ray image for the desired accuracy.

However, an 8-bit code word length is required only to construct a rotation-invariant code for the required number of markings, so that the reading direction and the orientation of the calibration phantom in the X-ray apparatus can be determined. If the orientation of the calibration phantom is known from the determination of the reading direction, it is sufficient for the code sequence to allow unique identification of the individual markings for the defined reading direction. The requirement that each code word occurs once, and only once, for both reading directions can thus be reduced to the requirement that each code word is in each case unique within only one reading direction.

The marker coding in one particularly advantageous embodiment of the present invention is thus based on a rotation-invariant 8-bit code sequence in which a 7-bit code sequence is integrated, whose individual code words occur once, and only once, within each reading direction. The following code sequence provides one example of such an 8-bit code sequence with 7-bit invariance:
000000010001010011000111110100011010100000011100 1101110001001 1101011011
00001011001001010101111001011101111111
The inverse code, the reflected code and the reflected inverse code derived from this also satisfy the requirements, of course.

An 8-bit code word need be read only once for evaluation, in order to determine the reading direction. For the further identification of the markings, it is thus sufficient to evaluate the superimposed 7-bit code, so that the identification of the individual markings is associated with reduced computation complexity. If the orientation of the calibration phantom is known or defined by a user, then it is possible in this case as well to dispense with the evaluation of the 8-bit code in favor of the superimposed 7-bit code.

The number of markings in the calibration phantom is not of fixed predetermined size, but is influenced by a number of factors, such as the size of the image area, the desired accuracy for determining a projection geometry and the relative extent of the calibration phantom with respect to the projection area of the X-ray system that is to be calibrated. If the number of markings is increased beyond the described level, codings must be used which are based on code words with a greater bit length, for example 9 bits or more.

The characteristics of the code sequences which have been developed for the described binary system and based on the described development criteria can, of course, also be transferred to systems which are based on three or more numbers. A ternary system with the numbers '0', '1'and '2' can be implemented, for example, using balls with three different diameters, in which case, in one specific embodiment, the number '0' is associated with the small-diameter balls, the number '1' is associated with the medium-diameter balls, and the number '2' is associated with the large-diameter balls.

The calibration phantom according to the invention allows identification of the image of a marking from a subsegment of the marking arrangement, so that there is no need for cohesive imaging of a marker chain. The coding sequence which is applied to the marker chain can be designed appropriately with regard to the achievable calibration accuracy, matching of the calibration phantom to the X-ray image size, simplicity in the positioning of the calibration phantom and the like.

What is claimed is:

1. A calibration phantom (20) for determining at least one projection geometry of X-ray apparatuses which are designed for recording radiographic projection images of objects for a representation of the objects which is derived from this with the aid of a reconstructive imaging method, the calibration phantom comprising a support (22) in the form of a defined volume body or hollow body and markings (15, 24, 25), which are applied in a linear arrangement (23) to the surface and/or within the support (22), the markings (15, 24, 25) having a first X-ray absorption capability and the support (22) having a second X-ray absorption capability, which is different from the first X-ray absorption capability, the linear arrangement (23) of the markings (15, 24, 25) precluding superimposition of an image of a first marking with an image of a second marking for a sufficient number of successive markings for each projection condition, the physical embodiment of a marking (15, 24, 25) representing a value assignment, and the value assignments for a sequence of successive markings (15, 24, 25) forming code information, wherein a first number of successive markings (15, 24, 25) form a first type of code information, with each code information item of the first type occurring once, and only once, in both sequence directions of the markings (15, 24, 25), and thus being unique.

2. The calibration phantom as claimed in claim 1, wherein a second number of successive markings (15, 24, 25) form a second type of code information.

3. The calibration phantom as claimed in claim 2, wherein each of the code information items of the second type occurs once, and only once, in one of the two sequence directions of the markings (15, 24, 25), and is thus unique.

4. The calibration phantom as claimed in claim 1, wherein the markings (15, 24, 25) have two different physical embodiments for a binary value assignment.

5. The calibration phantom as claimed in claim 1, wherein the physical extent of a marking (15, 24, 25) represents the value-assigning physical embodiment of the marking (15, 24, 25).

6. The calibration phantom as claimed in claim 1, wherein a marking (15, 24, 25) is in the form of a body with a spherical surface.

7. The calibration phantom as claimed in claim 1, wherein the support (22) is cylindrical.

8. The calibration phantom as claimed in claim 1, wherein the markings (15, 24, 25) are arranged along a helical line (23).

9. The calibration phantom as claimed in claim 1, wherein the markings (15, 24, 25) are so closely adjacent that at least one code information item of the first type is imaged in a radiographic projection image (12).

10. The calibration phantom as claimed in claim 1, wherein the extent of the physical distribution of the markings (15, 24, 25) exceeds the projection area, at least in a dimension transversely with respect to the projection direction.

11. A method for determining at least one projection geometry for an X-ray apparatus which is designed using a calibration phantom (20) as claimed in one claim 1 for recording radiographic projection images of objects for a representation of the objects which is derived from this with the aid of a reconstructive imaging process, the method comprising the following steps:

placing the calibration phantom (20) in the projection area between the X-ray source (11) and the detector (12), recording the projection images (12) in different projection conditions, determining the position of each image (16) of a marking (15, 24, 25) in each projection image (12), extracting the code information from the images (16) of the markings (15, 24, 25), identifying that marking which causes the image for each image of a marking with the aid of the extracted code information, and calculating the parameters of the projection geometry from the association between the images (16) of the markings (15, 24, 25) and the position of the markings (15, 24, 25) which cause them.

12. A calibration device for determining at least one projection geometry of an X-ray apparatus which is designed for recording radiographic projection images of objects for a representation of the objects which is derived from this with the aid of a reconstructive imaging method, the calibration device comprising a calibration phantom (20) as claimed in claim 1, a holding device (17) for placing the calibration phantom in the projection area of the X-ray apparatus (10), and an evaluation device (18) for carrying out a method for determining the projection geometry.

13. The calibration phantom as claimed in claim 2, wherein the markings (15, 24, 25) have two different physical embodiments for a binary value assignment.

14. The calibration phantom as claimed in claim 3, wherein the markings (15, 24, 25) have two different physical embodiments for a binary value assignment.

15. The calibration phantom as claimed in claim 2, wherein the physical extent of a marking (15, 24, 25) represents the value-assigning physical embodiment of the marking (15, 24, 25).

16. The calibration phantom as claimed in claim 3, wherein the physical extent of a marking (15, 24, 25) represents the value-assigning physical embodiment of the marking (15, 24, 25).

17. The calibration phantom as claimed in claim 4, wherein the physical extent of a marking (15, 24, 25) represents the value-assigning physical embodiment of the marking (15, 24, 25).

* * * * *